United States Patent
Brazdil et al.

(10) Patent No.: US 12,281,067 B2
(45) Date of Patent: Apr. 22, 2025

(54) DEHYDRATION AND CRACKING OF ALPHA-, BETA-DIHYDROXY CARBONYL COMPOUNDS TO LACTIC ACID AND OTHER PRODUCTS

(71) Applicant: Archer Daniels Midland Company, Decatur, IL (US)

(72) Inventors: James Brazdil, Glen Ellyn, IL (US); Donald Rogness, Del Mar, CA (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 576 days.

(21) Appl. No.: 17/046,738

(22) PCT Filed: Apr. 3, 2019

(86) PCT No.: PCT/US2019/025565
§ 371 (c)(1),
(2) Date: Oct. 9, 2020

(87) PCT Pub. No.: WO2019/199540
PCT Pub. Date: Oct. 17, 2019

(65) Prior Publication Data
US 2021/0163394 A1    Jun. 3, 2021

Related U.S. Application Data

(60) Provisional application No. 62/657,409, filed on Apr. 13, 2018.

(51) Int. Cl.
| | |
|---|---|
| *C07C 51/377* | (2006.01) |
| *C07C 29/60* | (2006.01) |
| *C07C 31/20* | (2006.01) |
| *C07C 31/22* | (2006.01) |
| *C07C 45/29* | (2006.01) |
| *C07C 59/08* | (2006.01) |
| *C07C 59/19* | (2006.01) |

(52) U.S. Cl.
CPC ............ *C07C 51/377* (2013.01); *C07C 29/60* (2013.01); *C07C 45/29* (2013.01); *C07C 31/202* (2013.01); *C07C 31/225* (2013.01); *C07C 59/08* (2013.01); *C07C 59/19* (2013.01)

(58) Field of Classification Search
CPC ....... C07C 51/377; C07C 59/08; C07C 59/19; C07C 29/00; C07C 31/202; C07C 29/60; C07C 31/205; C07C 31/225
USPC ....................................... 562/512
See application file for complete search history.

(56) References Cited

PUBLICATIONS

Kishida et al. Carbohydrate Research 341 (2006) 2619-2623.*
Yang et al. Biotechnology and Bioprocess Engineering (2017), 22(4), 376-381 2623.*
Marsh et al. Analytical Biochemistry, 145, 266-272, 1985.*

* cited by examiner

*Primary Examiner* — Ana Z Muresan
(74) *Attorney, Agent, or Firm* — Jesse S. Harper

(57) ABSTRACT

Processes are disclosed for the synthesis of a cracked product or an end product, from a starting compound or substrate having a carbonyl functional group (C=O), with hydroxy-substituted carbon atoms at alpha ($\alpha$) and beta ($\beta$) positions, relative to the carbonyl functional group. According a particular embodiment, an $\alpha$-, $\beta$-dihydroxy carboxylic acid or carboxylate is dehydrated to form a dicarbonyl intermediate by transformation of the $\alpha$-hydroxy group to a second carbonyl group and removal of the $\beta$-hydroxy group. The dicarbonyl intermediate is cracked to form the cracked product, in which the first and second carbonyl groups are preserved. Either or both of (i) the cracked product and (ii) a second cracked product generated from cleavage of a carbon-carbon bond of the dicarbonyl intermediate, may be further converted (e.g., by hydrogenation) to one or more end products, which, like the cracked product(s), also having fewer carbon atoms relative to the dicarbonyl intermediate and substrate.

6 Claims, 1 Drawing Sheet

DEHYDRATION AND CRACKING OF ALPHA-, BETA-DIHYDROXY CARBONYL COMPOUNDS TO LACTIC ACID AND OTHER PRODUCTS

CROSS-REFERENCE TO RELATED APPLICATIONS

This application is a national stage entry of International Application No. PCT/US19/25565, filed Apr. 3, 2019, which itself claims priority to U.S. Provisional Patent Application No. 62/657,409, filed Apr. 13, 2018, the contents of each are incorporated herein by reference.

FIELD OF THE INVENTION

The present invention relates to methods for synthesizing cracked products, including pyruvic acid and glyceraldehyde as precursors for a number of high value end products, with the cracked products and end products having a lower number of carbon atoms, relative to α-, β-dihydroxy carbonyl starting compounds, including α-, β-dihydroxy carboxylic acids and carboxylates such as products obtained from glucose.

BACKGROUND OF THE INVENTION

The depletion of fossil fuels has created major incentives for seeking alternative sources to petroleum-based carbon for the production of so-called "platform" molecules having low numbers of carbon atoms, such as propylene glycol and other 3 carbon atom-numbered ($C_3$) products. Biomass is currently viewed as a potential replacement from which many such known, high value petroleum-based chemicals can be derived, but the development of sustainable technologies for the production of such chemicals from renewable resources remains a significant challenge. In recent years, the biodiesel industry has provided abundant crude glycerol as a byproduct of refining triglycerides in plant oils and animal fats. This glycerol can serve as a feedstock for producing these same lower carbon number high value chemicals, such as propylene glycol. However, significant expense resides in the steps needed to adequately purify glycerol for this purpose, and the biodiesel industry is heavily dependent on tax credits and other forms of governmental subsidies for its profitability.

The present state of the art would benefit significantly from synthesis pathways to high value intermediates such as pyruvic acid and glyceraldehyde and/or downstream conversion products such as lactic acid, glycerol, and propylene glycol, from readily available or obtainable substrates and, in particular, from substrates which derive from renewable carbohydrate-based resources.

SUMMARY

Aspects of the invention are associated with the discovery of synthesis methods that can utilize substrates such as gluconic acid and glucaric acid, which are readily derived, for example from the oxidation of glucose. Advantageously, in the case of such carboxylate (carboxylic acid) substrates or starting compounds, they may potentially exhibit greater stability compared to their precursor aldehydes (e.g., glucose). Under high temperature reaction conditions, this stability can lead to increased reaction selectivity and yield along a desired reaction sequence leading to the production of one or more defined products. Product losses due to undesired side reactions are thereby reduced. Products of particular interest include "cracked" products formed from carbon-carbon bond cleavage and thereby having a lower number of carbon atoms relative to the substrate used. Obtaining suitable substrates from the oxidation of aldehyde precursors to carboxylates is straightforward and inexpensive, generally requiring only air as an oxidizing agent. Particular aspects are associated with the ability of the carboxylate anion-containing substrates to undergo a series of reaction steps in solution, leading to the formation of desirable 3 carbon atom-numbered cracked products such as pyruvic acid and glyceraldehyde, which may be further converted under the same reaction conditions (e.g., by hydrogenation/reduction) to desirable end products such as lactic acid, glycerol, and even propylene glycol (1,2-propanediol).

Particular aspects relate to synthesis pathways that utilize a cracking step, following the formation of a dicarbonyl intermediate from a starting compound that may be characterized as an α-, β-dihydroxycarbonyl compound. The cracking can be promoted using a cracking catalyst, under reaction conditions as described herein. Lower carbon atom-numbered cracked products include, for example, 3 carbon atom-numbered compounds, such as those described above, that may be synthesized from any of 4-, 5-, or 6-carbon atom-numbered substrates or starting compounds. Such substrates can, for example, commonly form pyruvic acid as a cracked product. More particular aspects relate to the discovery of such synthesis pathways, or individual reaction steps of such pathways, which may be performed non-enzymatically, meaning without the use of an enzyme (e.g., a polypeptide) in the reaction mixture. In the case of methods described herein being carried out non-enzymatically, such as using solely one or more chemical catalysts as opposed to biological catalyst(s), advantages reside in terms of allowing a wider range of possible reaction conditions, such as conditions of temperature and/or pH that would be detrimental to biological agents (e.g., would denature proteins including enzymes) but that nonetheless allow high productivities of a desired intermediate and/or end product. Other advantages may result from decreased operating costs, and particularly those otherwise associated with enzyme separation from the product, compared to the relatively lower costs associated with heterogeneous or homogeneous chemical catalyst separation. According to some embodiments, at least one of the synthesis steps described herein of (i) dehydrating the starting compound to form the dicarbonyl intermediate, (ii) cracking the dicarbonyl intermediate to produce the cracked product, (iii) hydrogenating the cracked product to produce an end product, and (iv) converting a second cracked product to an additional amount of the end product, is a non-enzymatic reaction step (i.e., is not catalyzed using an enzyme). Preferably, at least two of (i), (ii), (iii), and (iv) are non-enzymatic reaction steps, more preferably at least three of (i), (ii), (iii), and (iv) are non-enzymatic reaction steps, and still more preferably all of (i), (ii), (iii), and (iv) are non-enzymatic reaction steps.

Embodiments of the invention relate to methods for the synthesis of a cracked product, having a lower number of carbon atoms relative to a starting compound. The starting compound or substrate includes a carbonyl functional group (C=O), with hydroxy-substituted carbon atoms at alpha (α) and beta (β) positions, relative to the carbonyl functional group. According to one reaction step, this starting compound, namely an α-, β-dihydroxy carbonyl compound, i.e., a general class of compounds that embraces α-, β-dihydroxy carboxylic acids and carboxylates, is dehydrated to form a dicarbonyl intermediate by transformation of the α-hydroxy group to a second carbonyl group (adjacent a carbonyl group of the starting compound) and removal of the β-hydroxy group. The dicarbonyl intermediate is then cracked to form a cracked product, which is itself a dicarbonyl compound, but having fewer carbon atoms relative to the dicarbonyl intermediate and preserving the first and second carbonyl groups. This cracking generally leads to the production of a second cracked product, such as an aldehyde or carboxylate, which is different from the cracked (dicarbonyl) product. Often, in the case of 6 carbon atom-numbered substrates, both the cracked (dicarbonyl) product and second cracked (e.g., aldehyde or carboxylate) product may be 3 carbon atom-numbered products, such as glyceraldehyde or 2-hydroxy-3-oxopropanoic acid. In the case of 5 carbon atom-numbered substrates, the cracked (dicarbonyl) product may be a 3 carbon atom-numbered product and the second cracked (e.g., aldehyde or carboxylate) product may be a 2 carbon atom-numbered product, such as 2-hydroxyacetaldehyde or 2-oxoacetic acid. In the case of 4 carbon atom-numbered substrates, the cracked (dicarbonyl) product may be a 3 carbon atom-numbered product and the second cracked (e.g., aldehyde or carboxylate) product may be a single carbon atom-numbered product, such as formaldehyde or formic acid.

Either or both of the cracked product and second cracked product may be further converted, such as by hydrogenation/reduction under reducing conditions (e.g., elevated hydrogen partial pressure) that may be present in the reaction environment, to hydrogenated end products. Such hydrogenated end products, in the case of pyruvic acid as a cracked (dicarbonyl) product may include lactic acid, or, in the case of glyceraldehyde or 2-hydroxy-3-oxopropanoic acid as a second cracked (e.g., aldehyde or carboxylate) product, may include glycerol or glyceric acid, respectively. Other valuable end products may include lactic acid produced from glyceraldehyde through reactions involving a 1,2-hydride shift or a hydride transfer (Cannizzaro reaction).

These and other aspects, embodiments, and associated advantages will become apparent from the following Detailed Description.

Figure 1:
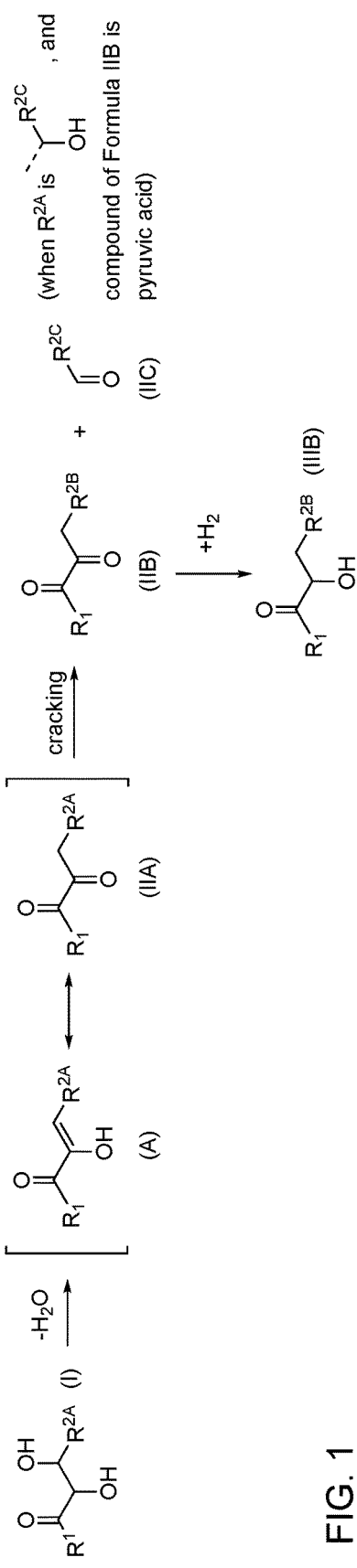
FIG. 1 illustrates a general reaction mechanism, comprising steps for synthesizing cracked products and end products according to synthesis methods described herein.

The figures are to be understood to present embodiments of the invention to aid in understanding of the principles and reaction chemistry involved, but not to limit the scope of the invention as defined in the appended claims. As would be apparent to one of skill in the art having knowledge of the present disclosure, synthesis methods according to various other embodiments of the invention will utilize particular reagents and reaction conditions determined, at least in part, according to specific objectives.

DETAILED DESCRIPTION OF EMBODIMENTS

As used herein, the term "substrate," or alternatively, "starting compound," refers to the initial compound that is subjected to one or preferably a series of conversion steps, such as "dehydrating," "cracking," and optional "hydrogenating" conversion steps, to yield one or more cracked products and/or end products. These conversion steps do not preclude the use of prior conversion steps, such as under the same reaction conditions (e.g., in the same reactor) or under different reaction conditions (e.g., in a separate reactor), as used to produce the cracked products and/or end products. Such prior conversion steps can include the conversion of a readily available precursor, such as glucose, to gluconic acid or glucaric acid as the starting compound, such as by oxidation. Likewise, steps performed "to produce a cracked product" or "to produce an end product" do not preclude the use of subsequent conversion steps, such as under the same reaction conditions (e.g., in the same reactor) or under different reaction conditions (e.g., in a separate reactor), as used to produce the cracked product(s) and/or end product(s), to obtain one or more other desired end products. For example, lactic acid as a hydrogenated end product may undergo further conversion to propylene glycol or acrylic acid. Glyceric acid as a hydrogenated end product may undergo further conversion to glycerol.

The terms "mol-%" and "wt-%" are used to designate amounts or concentrations in terms of percent by mole and percent by weight, respectively. Product yields given in terms of "mol-%" refer to the moles a given product (e.g., a cracked product such as pyruvic acid) obtained, based on the moles of substrate used (introduced or fed to the reactor).

The term "alkyl," when used alone or in combination with other moieties, for example, when used in combination in "alkoxy," "alkoxyalkyl," "hydroxyalkyl," "carboxyalkyl," "alkanoyl," and "alkanoylalkyl," represents a hydrocarbon moiety that is derived from an alkane. When used alone, "alkyl" therefore includes "methyl" ($CH_3$—), "ethyl" ($C_2H_5$—), etc. When used in combination, the alkyl portion of the moiety "alkoxy" is bonded at an end of the moiety to the rest of the molecule, through an intervening oxygen linkage, —O—, such as in the case of "methoxy" ($CH_3$—O—), "ethoxy" ($C_2H_5$—O—), etc., which terms are encompassed by "alkoxy." The alkyl portion of the moiety "alkanoyl" is bonded at an end of the moiety to the rest of the molecule, through an intervening carbonyl linkage, —(C=O)—, with "methanoyl" (HC=O—) representing a terminal aldehyde moiety, "ethanoyl" ($CH_3$—(C=O)—), representing methyl bonded through a carbonyl linkage, etc., which terms are encompassed by "alkanoyl."

The term "hydroxy" represents the moiety —OH, and the term "carboxy" represents the moiety —(C=O)OH. The term "hydroxyalkyl" represents hydroxy bonded at the end of the moiety to the rest of the molecule, through an intervening divalent alkyl portion, such as in the case of "hydroxymethyl" (HO—$CH_2$—), "hydroxyethyl" (HO—$C_2H_5$—), etc., which terms are encompassed by "hydroxyalkyl." The term "carboxyalkyl" represents carboxy bonded at the end of the moiety to the rest of the molecule, through an intervening divalent alkyl portion, such as in the case of "carboxymethyl" (HO—(C=O)—$CH_2$—), "carboxyethyl" (HO—(C=O)—$C_2H_5$—), etc., which terms are encompassed by "carboxyalkyl." The term "alkoxyalkyl" includes both a terminal alkoxy portion (i.e., bonded at the end of the moiety), as defined above and indicated by the designation "alkoxy," as well as an intervening divalent alkyl portion, through which "alkoxy" is bonded to the rest of the molecule. Therefore, "alkoxyalkyl" encompasses "methoxymethyl" ($CH_3$—O—$CH_2$—), "methoxyethyl" ($CH_3$—O—$C_2H_4$—), "ethoxymethyl" ($C_2H_5$—O—$CH_2$—), "ethoxyethyl" ($C_2H_5$—O—$C_2H_4$—), etc. The term "alkanoylalkyl" includes both a terminal alkanoyl portion (i.e., bonded at the end of the moiety), as defined above and indicated by the designation "alkanoyl," as well as an intervening divalent alkyl portion, through which "alkanoyl" is bonded to the rest of the molecule. Therefore, "alkanoylalkyl" encompasses "methanoylmethyl" (H(C=O)—CH$_2$—), "methanoylethyl" (H(C=O)—C$_2$H$_4$—), "ethanoylmethyl" (CH$_3$—(C=O)—CH$_2$—), "ethanoylethyl" (CH$_3$—(C=O)—C$_2$H$_4$—), etc.

The term "optionally substituted" with respect to "alkyl," or with respect to either terminal or intervening alkyl portions of moieties as defined above, is meant to encompass the substitution of a hydrogen substituent at one or more carbon-hydrogen bonds of the alkyl or alkyl portion with the designated substituent. In the case of a substituent of hydroxy (—OH) or methyl (—CH$_3$), one, two, or three hydrogen substituents at carbon-hydrogen bonds of a terminal alkyl carbon atom may be substituted with respective —OH and/or —CH$_3$ substituents, and one or two hydrogen substituents at carbon-hydrogen bonds of an intervening (alkylene) alkyl carbon atom may be substituted with respective —OH and/or —CH$_3$ substituents. For example, in the case of a terminal alkyl portion, its terminal carbon atom may be substituted with two —CH$_3$ substituents, to yield a terminal isopropyl moiety, or may be substituted with three —CH$_3$ substituents, to yield a terminal t-butyl moiety. In the case of an intervening alkyl portion, or an intervening carbon atom of a terminal alkyl portion, one or two hydrogen substituents at carbon-hydrogen bonds of an alkylene carbon atom may be substituted with —CH$_3$ substituents to yield the corresponding methyl-substituted or dimethyl-substituted derivatives. From this description, analogous substitutions of a terminal alkyl carbon atom or intervening alkyl carbon atom with one or more —OH substituents can be appreciated. In the case of a substituent of carbonyl (=O), hydrogen substituents at two carbon-hydrogen bonds of either a terminal alkyl carbon atom or an intervening (alkylene) alkyl carbon atom may be substituted with =O, to yield a terminal aldehyde moiety (or group) or a carbonyl moiety (or group), respectively.

In view of the possible moieties and the manner in which they may be substituted, it is recognized that there may be overlap in moiety definitions, for example in the case of "methanoyl" and a terminal "methyl" being substituted with =O, both of which represent a terminal aldehyde moiety (or group). Specific moieties are mentioned, however, in order to emphasize their positive inclusion in a given compound. In addition, when "alkyl" or an "alkyl portion" is further defined with respect to its corresponding number of carbon atoms (e.g., alkyl or an alkyl portion "having from 1 to 5 carbon atoms"), optional —CH$_3$ substituents, when present, are not included in this number of carbon atoms. That is, the phrase "having from 1 to 5 carbon atoms," and other phrases defining the number of alkyl carbon atoms, refer to a backbone number of alkyl carbon atoms that may be further substituted with —CH$_3$ substituents or other substituents, according to the specific definitions given.

Carboxylic acid compounds include their corresponding salt forms. In the case of a starting compound or substrate bearing a carboxylic acid functional group, the salt form is normally used in aqueous solution for carrying out the synthesis methods described herein. Corresponding salt forms of carboxylic acid include, for example, salts of alkali metals (e.g., the sodium salt form), salts of alkaline earth metals (e.g., the calcium salt form), and ammonium salts. Therefore, compounds such as "gluconic acid," "glucaric acid," "tartaric acid," "pyruvic acid," "lactic acid," "2-hydroxy-3-oxopropanoic acid," "glyceric acid," etc. are meant to encompass salt forms of "gluconate," "glucarate," "tartarate," "pyruvate," "lactate," "2-hydroxy-3-oxopropanoate," "glycerate," etc. Both generic and specific structures illustrating carboxylic acid compounds are likewise meant to encompass their salt forms or ionized forms, such that the structure of gluconic acid, for example, when shown with its carboxyl group un-ionized, is meant to encompass the structure with its carboxyl group ionized, and vice versa, with the un-ionized and ionized carboxyl group of the equivalent structures of this compound shown below:

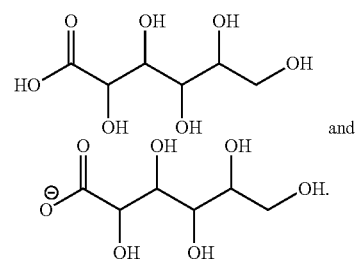

Compounds can possess one or more stereocenters, and structures are illustrated without regard for any specific stereochemistry, with the understanding that the reactions described with respect to substrates such as "gluconic acid," "glucaric acid," and "erythronic acid," which according to their nomenclature designate a specific stereochemistry, may be likewise carried out in an analogous manner with the respective, non-stereospecific substrates of "2,3,4,5,6-pentahydroxyhexanoic acid," "2,3,4,5-tetrahydroxyhexanedioic acid," and "2,3,4-trihydroxybutanoic acid," as well as with all stereoisomers of such compounds. Therefore, unless otherwise specified, "gluconic acid" is intended to encompass "gluconic acid and stereoisomers thereof," as is intended with respect to other compounds designating a specific stereochemistry. Generic and specific compounds described herein may be used or obtained in the form of pure or purified (enriched) optical isomers or otherwise in the form of racemic mixtures thereof. The use of optically active substrates or starting compounds may result in the formation of optically active products, using the synthesis methods described herein, as would be appreciated by those having skill in the art, combined with knowledge from the present disclosure. If desired, the purification of a particular optical isomer, or enrichment in one optical isomer relative to another, can be obtained, for example, by the formation of diastereomeric salts through treatment with an optically active acid or base. Examples of appropriate acids are tartaric, diacetyltartaric, dibenzoyltartaric, ditoluoyltartaric and camphorsulfonic acid. Examples of appropriate bases are plant-derived chiral alkaloids. The mixtures of diastereomers are then separated by crystallization, followed by liberation of the optically active bases or acids from these salts. A different process for separation of optical isomers involves the use of a chiral chromatography column chosen to maximize the separation of the enantiomers. Still another available method involves synthesis of covalent diastereomeric molecules by reaction with an optically pure acid in an activated form or an optically pure isocyanate. The synthesized diastereomers can be separated by conventional means such as chromatography, distillation, crystallization or sublimation, and then hydrolyzed to yield the enantiomerically pure compound.

A general reaction mechanism for synthesizing cracked products and end products is illustrated in FIG. 1. As shown, a starting material of general Formula I is broadly an α-, β-dihydroxy carbonyl compound, which encompasses a preferred class of compounds, namely α-, β-dihydroxy carboxylates when $R^1$ is hydroxy (—OH) to provide a terminal carboxyl group on the left-hand side of the illustrated compound. A starting material of general Formula I in FIG. 1 comprises an α-hydroxy group, substituted at the α-carbon atom with respect to the carbonyl (C=O) group shown, as well as a β-hydroxy group, substituted at the β-carbon atom with respect to this carbonyl group. According to the illustrated synthesis mechanism, a first step of dehydration (water removal) causes removal of the β-hydroxy group, together with formation of a site of unsaturation, i.e., a carbon-carbon double bond between the α-carbon atom and the β-carbon atom. The resulting ethylenically unsaturated, dehydrated compound, shown as compound A, tends to maintain tautomeric equilibrium with the dicarbonyl intermediate shown as having general Formula IIA. The dehydrating step may therefore comprise forming water from a combination of the β-hydroxy group and hydrogen of the α-hydroxy group, in a starting compound or substrate of general Formula I.

The dicarbonyl intermediate compound of general Formula IIA may then undergo cracking to form the cracked product of general Formula IIB. As a consequence of cracking, the moiety represented by $R^{2B}$ in this cracked product has fewer carbon atoms relative to the moiety represented by $R^{2A}$ in the dicarbonyl intermediate of general Formula IIA. Accordingly, the cracked product overall has fewer carbon atoms relative to this dicarbonyl intermediate. Optional hydrogenation of the cracked product can then produce an end product, in this case a corresponding hydrogenated end product having the general Formula IIIB as shown in FIG. 1. Cracking to form the cracked product additionally forms a second cracked product having the general Formula IIC and therefore having an aldehyde group. Depending on the substrate or starting compound, this second cracked product may include other functional groups, such as a carboxylic acid functional group, as the moiety represented by $R^{2C}$, or otherwise included in a terminal portion of this moiety, which is bonded to the aldehyde functional group. Such a second cracked product may result, for example, when the moiety represented by $R^{2A}$ in the dicarbonyl intermediate of general Formula IIA is bonded through a hydroxy-substituted carbon atom. That is, the starting compound may further comprise a gamma hydroxy group, substituted at a gamma carbon atom with respect to the first carbonyl group, such that the cracking forms, in addition to the first (dicarbonyl) cracked product, a second cracked product having an aldehyde group resulting from cleavage between a beta carbon atom and a gamma carbon atom of the dicarbonyl intermediate, corresponding to the beta carbon atom and the gamma carbon atom of the starting compound. In a particular embodiment, the second cracked product of general Formula IIC may result in the case of $R^{2A}$, or at least a terminal portion of $R^{2A}$, representing a moiety of

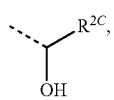

in which case the cracked product will have fewer carbon atoms, relative to both the dicarbonyl intermediate and the substrate. The cracked product may then optionally undergo hydrogenation, whereas further conversions of the second cracked product (e.g., also by hydrogenation) may form other desirable compounds, for example as described with respect to the more particular embodiment shown in FIG. 2. According to some methods, the moiety represented by $R^{2C}$ in the second cracked product, having the general Formula IIC, may have one fewer carbon atom, relative to the moiety represented by $R^{2A}$, and this second cracked product may represent a corresponding aldehyde or corresponding carboxylic acid formed from $R^{2A}$ and having the same number of carbon atoms as $R^{2A}$. In this case, the cracked product may be pyruvic acid, which may become hydrogenated to lactic acid. It can be appreciated, therefore, that a synthesis route to lactic acid, through cracking of the dicarbonyl intermediate to form pyruvic acid, can be carried out using a variety of α-, β-dihydroxy carbonyl compounds, including α-, β-dihydroxy carboxylic acids and carboxylates having at least four carbon atoms, as substrates.

Accordingly, representative methods may comprise, in addition to producing a cracked product that is a dicarbonyl compound, hydrogenating some or all of this cracked product to produce an end product that preserves the first carbonyl group of the starting compound and dicarbonyl intermediate, but further includes an adjacent hydroxy group, resulting from hydrogenation of the second carbonyl group of the cracked product. Consumption of the cracked product of general Formula IIB by its hydrogenation thereby drives the cracking reaction forward, ultimately resulting in the further production of the dicarbonyl compound from compound A, by shifting the tautomeric equilibrium in this direction. The rate at which the cracked (dicarbonyl) product becomes hydrogenated may be regulated by the use of an optional cracking catalyst, as well as reaction conditions, as described herein. As a result of the cracking step, a 3 carbon atom-numbered cracked product, such as pyruvic acid, may be produced from available 4-, 5-, or 6-carbon atom-numbered α-, β-dihydroxy carboxylic acids and carboxylates as starting compounds, such as erythronic acid (or 2,3,4-trihydroxybutanoic acid generally); 2,3-dihydroxy-4-oxobutanoic acid; tartaric acid; 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally). Representative synthesis methods may therefore comprise converting available $C_4$-$C_6$ substrates, such as readily available carbohydrates, to produce $C_3$ compounds as cracked products and end products. In such embodiments, if the substrate is a 6 carbon atom-numbered compound ($C_6$ substrate), then the second cracked product of the synthesis method is likewise a $C_3$ compound. For example, the 6 carbon atom-numbered substrates gluconic acid and glucaric acid may each produce pyruvic acid as a cracked product, and lactic acid as an end product of the hydrogenation of lactic acid. In the case of gluconic acid, the second cracked product may be glyceraldehyde, which may undergo hydrogenation to produce glycerol as an end product. In the case of glucaric acid, the second cracked product may be 2-hydroxy-3-oxopropanoic acid, which may undergo hydrogenation to produce glyceric acid as an end product.

With respect to compounds in FIG. 1 having the general Formulas I, IIA, IIB, and IIIB, as well as those having the general formula given for compound A, $R^1$ may be selected from the group consisting of alkyl, alkoxy, alkoxyalkyl, hydroxy, and hydroxyalkyl, wherein alkyl and the alkyl portions of alkoxy, alkoxyalkyl, and hydroxyalkyl have from 1 to 5 carbon atoms, optionally substituted with one or more substituents (i.e., may optionally have hydrogen substituents at carbon-hydrogen bonds substituted, as defined herein, with one or more substituents) selected from the group consisting of —OH, —CH$_3$, and =O. According to particular embodiments, in these respective compounds, including the starting compound of general Formula I, the dicarbonyl intermediate and cracked product of general Formulas IIA and IIB, respectively, and/or the end product of general Formula IIIB, R$^1$ may be alkyl (e.g., having from 1 to 3 alkyl carbon atoms) and may result in a terminal ketone functional group in the respective compounds; R$^1$ may be alkoxy (e.g., having from 1 to 3 alkyl carbon atoms) and may result in a terminal ester functional group in the respective compounds; or R$^1$ may be hydroxy and may result in a terminal carboxyl functional group in the respective compounds. Preferably, R$^1$ is hydroxy, whereby the starting compound and the dicarbonyl intermediate are carboxylic acids. For example, as described above with respect to terms used herein generally, the starting compound, the dicarbonyl intermediate, the cracked product, and/or the end product may be in the form of (e.g., present in the reaction mixture as) carboxylates, meaning compounds comprising a carboxylate anion and possibly present in salt form in an aqueous reaction mixture (e.g., in their corresponding ammonium salt form) that is used to carry out synthesis methods described herein.

With respect to compounds in FIG. 1 having the general Formulas I and IIA, as well as those having the general formula given for compound A, R$^{2,4}$ may be selected from the group consisting of alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 5 carbon atoms, optionally substituted with one or more substituents selected from the group consisting of —OH, —CH$_3$, and =O. According to a particular embodiment, R$^{2,4}$ may selected from the group consisting of alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 3 carbon atoms, optionally substituted with one or more of —OH and/or one or more of —CH$_3$. According to a more particular embodiment, R$^{2,4}$ may be alkyl, carboxy, carboxyalkyl, alkanoyl, or alkanoylalkyl, wherein alkyl and the alkyl portions of carboxyalkyl, alkanoyl, and alkanoylalkyl have from 1 to 3 carbons atoms, optionally substituted with one or more of —OH. Particular substrates having from 4-6 carbon atoms include erythronic acid (or 2,3,4-trihydroxybutanoic acid generally); 2,3-dihydroxy-4-oxobutanoic acid; tartaric acid; 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally).

In the case of a particular 4 carbon atom-numbered substrate, when R$^1$ is hydroxy and R$^{2,4}$ is hydroxymethyl, the starting compound is erythronic acid (or 2,3,4-trihydroxy butanoic acid generally). In this case, the cracking step may therefore produce pyruvic acid, in addition to a single carbon atom-numbered second cracked product such as formaldehyde. Hydrogenation of the cracked products would therefore result in lactic acid and methanol, respectively. This example, and other examples of 4- and 5-carbon numbered substrates and their corresponding cracked products, second cracked products, and hydrogenation products, are provided below in Table 1.

TABLE 1

Representative 4- and 5-carbon numbered substrates and their synthesis products

| R$^1$, Formula I | R$^{2,4}$, Formula I | Substrate | Cracked Product | Second Cracked Product | Hydrogenation Products |
|---|---|---|---|---|---|
| hydroxy | hydroxymethyl | erythronate, or 2,3,4-trihydroxy butanoate | pyruvate | formaldehyde | lactate, methanol |
| hydroxy | methanoyl | 2,3-dihydroxy-4-oxobutanoic acid | pyruvate | formic acid | lactate, methanol |
| hydroxy | carboxy | tartarate | pyruvate | formic acid | lactate, methanediol |
| hydroxy | 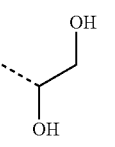 | 2,3,4,5-tetrahydroxy pentanoate | pyruvate | 2-hydroxy acetaldehyde | lactate, ethanediol |
| hydroxy | 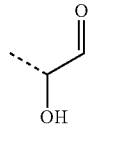 | 2,3,4-trihydroxy-5-oxopentanoate | pyruvate | oxalaldehyde | lactate, 2-hydroxy acetaldehyde |
| hydroxy |  | 2,3,4-trihydroxy pentanedioate | pyruvate | 2-oxoacetate | lactate, 2-hydroxyacetate |

Specific examples of 6 carbon-numbered substrates and their corresponding cracked products, second cracked products, and hydrogenation products, are described below in connection with substrates having the particular structures of Formulas IV and VI, being within the scope of Formula I.

With respect to compounds having the general Formulas IIB and IIIB, $R^{2B}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms, optionally substituted with one or more substituents selected from the group consisting of —OH, —CH$_3$, and =O. According to a particular embodiment, $R^{2B}$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 3 carbon atoms, optionally substituted with one or more of —OH and/or one or more of —CH$_3$. According to a more particular embodiment, $R^{2B}$ may be a hydrogen substituent, alkyl, carboxy, carboxyalkyl, alkanoyl, or alkanoylalkyl, wherein alkyl and the alkyl portions of carboxyalkyl, alkanoyl, and alkanoylalkyl have 1 or 2 carbons atoms, optionally substituted with one or more of —OH. According to another particular embodiment, $R^{2B}$ may be a hydrogen substituent or alkyl having from 1 to 3 carbon atoms, optionally substituted with one or more of —OH.

It can be further appreciated from the present disclosure that, when $R^1$ is hydroxy and $R^{2B}$ is a hydrogen substituent, the cracked product is pyruvic acid that may become hydrogenated to form lactic acid, potentially from a variety of possible α-, β-hydroxy carboxylate substrates, as described above. In addition, the second cracked product of general Formula IIC may result in the case of $R^{2A}$, or at least a terminal portion of $R^{2A}$, representing a moiety of

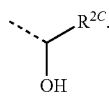

Accordingly, $R^{2C}$ in compounds of general Formula IIC may represent moieties as defined above with respect to $R^{2A}$, but having at least one fewer carbon atom. Therefore, $R^{2C}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms, optionally substituted with one or more substituents selected from the group consisting of —OH, —CH$_3$, and =O. According to a particular embodiment, $R^{2C}$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have one or two carbon atoms, optionally substituted with one or more of —OH and/or one or more of —CH$_3$. According to a more particular embodiment, $R^{2C}$ may be a hydrogen substituent or alkyl having one or two carbon atoms, optionally substituted with one or more of —OH.

In a more specific embodiment, the moiety $R^{2A}$ of compounds in FIG. 1 may represent

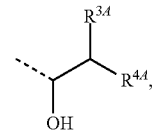

such that the starting compound and the dicarbonyl intermediate compound have general Formula IV and Formula VA, respectively:

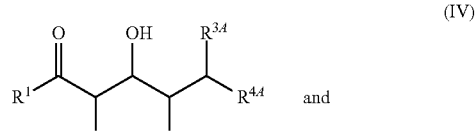

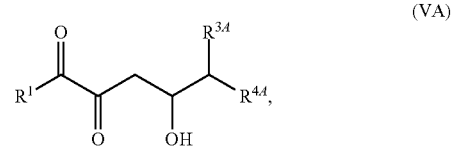

which compounds can optionally be in their respective salt forms, as described above. With respect to these compounds, $R^1$ may be as defined above. $R^{3A}$ may be selected from the group consisting of a hydrogen substituent, alkoxy, hydroxy, and carboxy, wherein the alkyl portion of alkoxy has from 1 to 5 carbon atoms which may optionally be substituted with one or more substituents selected from the group consisting of —OH, —CH$_3$, and =O. Preferably, $R^{3A}$ is a hydrogen substituent, methyl, methoxy, hydroxy, or carboxy. $R^{4A}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 5 carbon atoms which may optionally be substituted with one or more substituents selected from the group consisting of —OH, —CH$_3$, and =O. Preferably, $R^{4A}$ is a hydrogen substituent, methyl, methoxy, hydroxy, or carboxy.

In the case of a particular 6 carbon atom-numbered substrate, $R^1$ and $R^{3A}$ may both be hydroxy, and $R^{4A}$ may be carboxy, resulting in glucaric acid (or 2,3,4,5-tetrahydroxyhexanedioic acid generally) as the substrate of general Formula IV and 2-keto-3-deoxyglucaric acid (2,3-dihydroxy-5-oxohexanedioic acid) as the dicarbonyl intermediate of general Formula VA. In this case, the cracked product of general Formula IIB may be pyruvic acid, which may be hydrogenated to produce lactic acid as an end product of general Formula IIIB, as described above. The second cracked product of general Formula IIC may be 2-hydroxy-3-oxopropanoic acid, which may be hydrogenated to produce glyceric acid as described above. In the case of another particular 6 carbon atom-numbered substrate, $R^1$ and $R^{3A}$ may both be hydroxy, and $R^{4A}$ may be methanoyl, resulting in 2,3,4,5-tetrahydroxy-6-oxohexanoic acid as the substrate of general Formula IV and 4,5-dihydroxy-2,6-dioxohexanoic acid as the dicarbonyl intermediate of general Formula VA. In this case, the cracked product of general Formula IIB may be pyruvic acid, which may be hydrogenated to produce lactic acid as an end product of general Formula IIIB, as described above. The second cracked product of general Formula IIC may be 2-hydroxymalonaldehyde, which may be hydrogenated to produce glyceraldehyde.

According to still more particular embodiments, the moiety $R^{2A}$ of compounds in FIG. 1 may represent

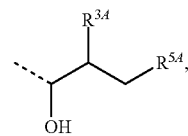

which is obtained when, in compounds of general Formula IV above, $R^{4A}$ comprises a methylene (—CH$_2$—) carbon atom, such that $R^{4A}$ may be selected from the group consisting of alkyl, alkoxyalkyl, hydroxyalkyl, carboxyalkyl, and alkanoylalkyl. According to such embodiments, it is possible for the starting compound of general Formula IV and the dicarbonyl intermediate compound of general Formula VA to have the more particular structures corresponding to general Formula VI and general Formula VIIA, respectively:

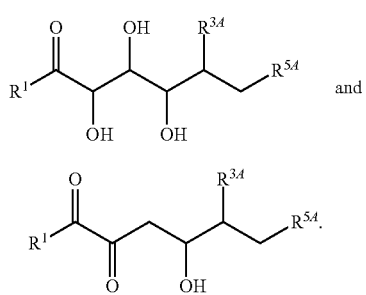

The moieties $R^1$ and $R^{3A}$ may be as defined above, and the moiety $R^{5A}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms which may optionally be substituted with one or more substituents selected from the group consisting of —OH, —CH$_3$, and =O. Preferably, $R^{5A}$ is a hydrogen substituent, methyl, methoxy, hydroxy, or carboxy.

In another example of a particular 6 carbon atom-numbered substrate, $R^1$, $R^{3A}$, and $R^{5A}$ may be hydroxy, resulting in gluconic acid (or 2,3,4,5,6-pentahydroxyhexanoic acid generally) as the substrate of general Formula VI and 2-keto-3-deoxygluconic acid (4,5,6-trihydroxy-2-oxohexanoic acid) as the dicarbonyl intermediate of general Formula VIIA. In this case, the cracked product of general Formula IIB may be pyruvic acid, which may be hydrogenated to produce lactic acid as an end product of general Formula IIIB, as described above. The second cracked product of general Formula IIC may be glyceraldehyde, which may be hydrogenated to produce glycerol as described above.

A typical reaction environment associated with the synthesis of a cracked product and/or an end product, according to methods described herein, includes an elevated hydrogen partial pressure, such as a hydrogen partial pressure of at least about 3 megapascals (MPa) (435 psi), optionally in combination with a hydrogenation catalyst. In this hydrogenating/reducing environment, the terminal aldehyde group in the second cracked product of general Formula IIC may be converted to a terminal alcohol or hydroxy (—OH) group. Other possible conversion products of the cracked product and second cracked product are possible, as described in greater detail below with respect to the more particular embodiment shown in FIG. 2.

Figure 2:
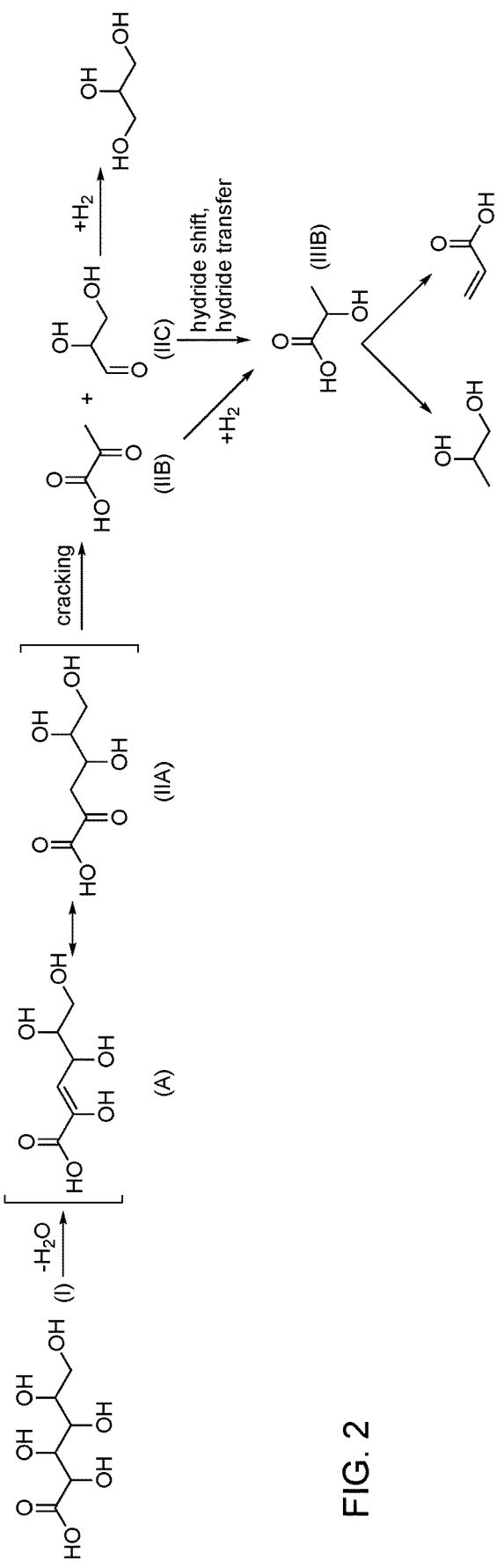
FIG. 2 illustrates a specific reaction mechanism, according to which gluconic acid is the starting material or substrate.

FIG. 2 illustrates the synthesis method presented in FIG. 1, using gluconic acid as a starting compound, or compound of Formula I, in which $R^{2A}$ represents the moiety

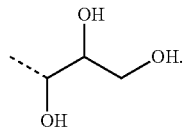

In this embodiment, the dicarbonyl intermediate of Formula IIA is 2-keto-3-deoxygluconic acid (2-keto-4,5,6-trihydroxyhexanoic acid), as shown. This dicarbonyl intermediate can then undergo cracking to yield a cracked product of Formula IIB, which in the embodiment illustrated in FIG. 2 is pyruvic acid. In addition, a second cracked product of Formula IIC is produced, which in this embodiment is glyceraldehyde, according to which $R^{2C}$ in the general formula for this compound as shown in FIG. 1, is a moiety of

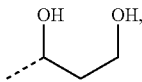

which corresponds to the moiety of $R^{2A}$ as shown above, but having one fewer carbon atom.

End product and further conversion products may also be formed under reaction conditions described herein, as shown in FIG. 2. For example, hydrogenation/reduction of pyruvic acid, the cracked product of Formula IIB, can yield lactic acid. Hydrogenation/reduction of glyceraldehyde, the second cracked product of Formula IIC, can yield glycerol, as shown. In addition, the glyceraldehyde produced can undergo further reactions, such as those involving a 1,2-hydride shift or a hydride transfer (Cannizzaro reaction) to cause its conversion to lactic acid, as shown in FIG. 2. Therefore, according to particular embodiments, lactic acid may be produced in a molar amount that exceeds the molar amount of glyceraldehyde produced, despite the fact that a first portion of this lactic acid may be derived from hydrogenation of pyruvic acid, which is produced via the cracking reaction in an equimolar amount with glyceraldehyde. That is, glyceraldehyde may be converted to a second portion of lactic acid, such that the reaction mixture may comprise a combined, first and second portion of lactic acid that exceeds, on a molar basis, the amount of glyceraldehyde. For example, the ratio of the total (combined) molar amount of lactic acid to the net molar amount of glyceraldehyde (e.g., in the reaction mixture after completion of a synthesis method), may be at least about 1.2, at least about 1.5, or at least about 2.0. This excess may result, at least in part, due to the conversion of glyceraldehyde to lactic acid. As also shown in FIG. 2, lactic acid may also react to produce propylene glycol and acrylic acid, as further conversion products, under reaction conditions described herein.

Representative methods are therefore described herein, for synthesizing an α-hydroxy carboxylate end product having a lower number of carbon atoms relative to an α-, β-dihydroxy carboxylate starting compound. The methods comprise reacting an α-, β-dihydroxy carboxylate starting compound in a reaction mixture that preferably comprises a cracking catalyst, i.e., a catalyst or promoter of the reaction step shown as "cracking" in FIGS. 1 and 2. Preferred cracking catalysts comprise one or more cracking active metals, such as tungsten, molybdenum, and/or vanadium, which may be present in the form of corresponding salts in the reaction mixture, such as tungstate, molybdate, or vanadate salts, which include a metatungstate salt, a paratungstate salt, a metamolybdate salt, a paramolybdate salt, a metavanadate salt, or a paravanadate salt. Representative tungstate salts are salts of Group 1 (alkali) metals or Group 2 (alkaline earth) metals, as well as ammonium salts. Ammonium metatungstate and ammonium paratungstate salts are representative. A cracking catalyst (e.g., ammonium metatungstate) may be present in the reaction mixture in an amount of from about 0.1 mol-% to about 30 mol-%, from about 0.5 mol-% to about 10 mol-%, or from about 1 mol-% to about 5 mol-%, relative to the number of moles of substrate, for example according to the initial reactor loading composition in the case of a batchwise reaction or according to a steady-state composition in the case of a continuous reaction. The cracking catalyst may also, or may alternatively, be present in the reaction mixture in an amount such that the moles of cracking active metal (e.g., tungsten, molybdenum, or vanadium) may represent from about 6 mol-% to about 50 mol-%, or from about 10 mol-% to about 35 mol-%, relative to the number of moles of substrate. Other cracking catalysts can include solid acids and/or Lewis acids (e.g., organometallic compounds, including organotin compounds).

According to these methods the α-hydroxy carboxylate end product, such as lactic acid, is formed from a combination of cracking and hydrogenation. Further aspects of the invention relate to the discovery that the use of a base, such as a hydroxide, can promote the conversion of at least a portion of a cracked aldehyde product, such as glyceraldehyde, to an additional amount of the end product. For example, glyceraldehyde can undergo further reactions, including those involving a 1,2-hydride shift or a hydride transfer (Cannizzaro reaction), such that it may be converted or isomerized to an additional amount of lactic acid. This additional amount of end product may be expressed relative to a baseline amount in which the base is absent, or otherwise present in a nominal amount. The additional amount of the end product may represent an increase of at least about 10 mol-%, at least about 20 mole-%, or at least about 50 mol-%, relative to the baseline amount. The reaction mixture may therefore comprise a base, such as a hydroxide, to promote the production of such additional amount of end product. Representative hydroxides include ammonium hydroxide, as well as alkali and alkaline earth metal hydroxides, such as lithium hydroxide, sodium hydroxide, potassium hydroxide, etc., with lithium hydroxide being preferred.

Particular methods are directed to the synthesis of lactic acid from an α-, β-dihydroxy carboxylate starting compound having greater than 3 carbon atoms, such as a salt of gluconate (or 2,3,4,5,6-pentahydroxyhexanoate generally); 2,3,4,5-tetrahydroxy-6-oxohexanoate; glucarate (or 2,3,4,5-tetrahydroxyhexanedioate generally); 2,3,4,5-tetrahydroxypentanoate; 2,3,4-trihydroxy-5-oxopentanoate; 2,3,4-trihydroxypentanedioate; erythronate (or 2,3,4-trihydroxybutanoate generally); 2,3-dihydroxy-4-oxobutanoate; or tartarate. As described herein, representative methods comprise dehydrating this starting compound to form a dicarbonyl intermediate by transformation of the alpha hydroxy group to a second carbonyl group and removal of the beta hydroxy group, and cracking this dicarbonyl intermediate by cleavage between a beta carbon atom and a gamma carbon atom of the dicarbonyl intermediate, corresponding to the beta carbon atom and the gamma carbon atom with respect to the carboxylate group of the starting compound, to form pyruvate. The methods further comprise hydrogenating or reducing the pyruvate to produce the lactic acid, and optionally further conversion products such as propylene glycol or acrylic acid.

According to particular embodiments the total yield(s) of the cracked product, second cracked product, or any particular end product and/or further conversion product as described herein, based on the theoretical yields proceeding through the respective pathways as also described herein, may be generally at least about 25 mol-% (e.g., from about 25 mol-% to about 90 mol-%), typically at least about 35 mol-% (e.g., from about 35 mol-% to about 80 mol-%), and often at least about 50 mol-% (e.g., from about 50 mol-% to about 75 mol-%). These yields can apply, for example, to (i) any cracked product of general Formula IIB, such as pyruvic acid or any other specific cracked product of this general formula, described herein, (ii) any second cracked product of general Formula IIC, such as glycerol or any other specific second cracked product of this general formula, described herein, (iii) any end product of general Formula IIIB, such as lactic acid or any other specific end product of this general formula, described herein, (iv) any end product resulting from conversion (e.g., hydrogenation) of the second cracked product of general Formula IIC, such as glycerol or any other such specific conversion product described herein, and/or (v) any further conversion product such as propylene glycol or acrylic acid, as described herein.

The reaction mixture, which is preferably an aqueous reaction mixture, may further comprise a hydrogenation catalyst, such as solid (heterogeneous) catalyst. A representative hydrogenation catalyst may comprise one or more hydrogenation active metals selected from Groups 8-11 of the Periodic Table, such as, for example, ruthenium (Ru), cobalt (Co), nickel (Ni), platinum (Pt), palladium (Pd), or gold (Au). A preferred hydrogenation active metal is ruthenium. The catalyst may further comprise a solid support of the hydrogenation active metal(s), with the metals being dispersed on the solid support according to a distribution, for example preferentially near the outer surface of the solid support or otherwise substantially uniformly throughout a porous solid support, depending on the particular catalyst preparation technique used (e.g., evaporative impregnation of a solution of the hydrogenation active metal). Preferably, the hydrogenation active metal, or such metals in combination, is/are present in an amount from about 1 wt-% to about 15 wt-%, or from about 2 wt-% to about 10 wt-%, based on the total weight of the hydrogenation catalyst.

The hydrogenation active metal(s) may be present in the reaction mixture in an amount such that the moles of hydrogenation active metal(s) (e.g., ruthenium) represent from about 1 mol-% to about 20 mol-%, or from about 2 mol-% to about 10 mol-%, relative to the number of moles of substrate, for example according to the initial reactor loading composition in the case of a batchwise reaction or according to steady-state composition in the case of a continuous reaction. The solid support is preferably refractory in the reaction mixture and under the synthesis reaction conditions described herein. Representative solid supports comprise one or more metal oxides, such as aluminum oxide (alumina), silicon oxide (silica), titanium oxide (titania), zirconium oxide (zirconia), magnesium oxide (magnesia), strontium oxide (strontia), etc. A preferred solid support is carbon. According to a particular embodiment, the hydrogenation catalyst comprises ruthenium on a carbon support, with the ruthenium being present in an amount within a range given above, based on total catalyst weight and/or within a range given above, relative to the number of moles of substrate.

Reaction conditions, under which the reaction mixture is maintained during the synthesis of the cracked product(s) and/or end product(s), include an elevated pressure and hydrogen partial pressure. Representative absolute reactor pressures are in the range generally from about 2.07 MPa (300 psi) to about 24.1 MPa (3500 psi), typically from about 3.45 MPa (500 psi) to about 20.7 MPa (3000 psi), and often from about 10.3 MPa (1500 psi) to about 17.2 MPa (2500 psi). The reactor pressure may be generated predominantly or substantially from hydrogen, such that these ranges of total pressure may also correspond to ranges of hydrogen partial pressure. However, the presence gaseous species vaporized from the reaction mixture, such as ammonia and/or water vapor, may result in the hydrogen partial pressure being reduced relative to these total pressures, such that, for example, the hydrogen partial pressure may range generally from about 1.38 MPa (200 psi) to about 22.4 MPa (3250 psi), typically from about 2.41 MPa (350 psi) to about 19.0 MPa (2750 psi), and often from about 8.62 MPa (1250 psi) to about 15.5 MPa (2250 psi).

Other reaction conditions include a temperature from about 100° C. to about 350° C., and preferably from about 130° C. to about 230° C. The reaction time, i.e., time at which the reaction mixture is maintained under conditions of pressure and temperature at any target values or target sub-ranges within any of the ranges of pressure and temperature given above (e.g., a target, total pressure value of 13.8 MPa (2000 psi) and a target temperature of 160° C.), is from about 0.5 hours to about 24 hours, and preferably from about 1 hour to about 5 hours, in the case of a batchwise reaction. For a continuous reaction, these reaction times correspond to reactor residence times. Continuous operation may be performed, for example, under the conditions of pressure and temperature described above, with continuous feeding of the substrate and hydrogen, and continuous withdrawal of the reaction mixture comprising the cracked product(s) and/or end product(s). Continuous operation may further include the continuous purification of the cracked products and/or end products, the continuous separation of process streams comprising unconverted gaseous and/or liquid products, and/or the continuous recycle of one or more of such process streams back to the reaction mixture, maintained in the synthesis reactor. In the case of recycle operation, the yields of the cracked product(s) and/or end product(s), as described above, will correspond to the "once-through" or "per-pass" yield, with higher overall yields being possible due to the recycle.

Overall, aspects of the invention relate to the use of synthesis methods described herein to produce cracked product(s), and/or end product(s) from readily available, or easily derived, substrates. The end products, and optionally further conversion products as described herein, may be produced from the further conversion of the cracked products (including second cracked products as described herein) either in situ or in a further, separate reaction stage. The cracked product(s) and/or end product(s) have a lower number of carbon atoms relative to the substrates used to produce these products. The methods may advantageously address various shortcomings of conventional methods. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modifications and/or substitutions without departing from the scope of this disclosure. The specific embodiments illustrated and described herein are for illustrative purposes only, and not limiting of the invention as set forth in the appended claims.

What is claimed is:

1. A method comprising:
   (a) dehydrating a starting compound in the form of glucaric acid or a salt thereof or a stereoisomer of glucaric acid or a salt thereof, to form a dicarbonyl intermediate of 2-keto-3-deoxyglucaric acid or a salt thereof or a stereoisomer of 2-keto-3-deoxyglucaric acid or a salt thereof by transformation of the alpha hydroxy group to a second carbonyl group and removal of the beta hydroxy group; and
   (b) cracking the dicarbonyl intermediate in the presence of a cracking catalyst comprising an active metal or a salt thereof to produce pyruvic acid or a salt thereof.

2. The method of claim 1, further comprising:
   (c) hydrogenating the pyruvic acid or a salt thereof to produce lactic acid or a salt thereof.

3. The method of claim 1, wherein cracking step (b) additionally forms a second cracked product in the form of 2-hydroxy-3-oxopropanoic acid or a salt thereof.

4. The method of claim 3, further comprising hydrogenating the 2-hydroxy-3-oxopropanoic acid or a salt thereof to glyceric acid or a salt thereof.

5. The method of claim 1, wherein the active metal comprises one or more of tungsten, molybdenum, and vanadium.

6. The method of claim 5, wherein the cracking catalyst is present in a reaction mixture, comprising the dicarbonyl intermediate of 2-keto-3-deoxyglucaric acid or a salt thereof or the stereoisomer of 2-keto-3-deoxyglucaric acid or a salt thereof, in an amount from about 0.1 mol-% to about 30 mol-%.

* * * * *